(12) United States Patent
Laustsen

(10) Patent No.: US 10,844,345 B2
(45) Date of Patent: Nov. 24, 2020

(54) HIGH DENSITY FILL AND DRAW FERMENTATION PROCESS

(71) Applicant: CMC BIOLOGICS A/S, Søborg (DK)

(72) Inventor: Mads Laustsen, Gentofte (DK)

(73) Assignee: CMC BIOLOGICS A/S, Soborg (DK)

( * ) Notice: Subject to any disclaimer, the term of this patent is extended or adjusted under 35 U.S.C. 154(b) by 0 days.

(21) Appl. No.: 15/303,735

(22) PCT Filed: Apr. 14, 2015

(86) PCT No.: PCT/EP2015/058037
§ 371 (c)(1),
(2) Date: Oct. 12, 2016

(87) PCT Pub. No.: WO2015/158696
PCT Pub. Date: Oct. 22, 2015

(65) Prior Publication Data
US 2017/0067010 A1    Mar. 9, 2017

(30) Foreign Application Priority Data
Apr. 16, 2014  (EP) .................................. 14164862

(51) Int. Cl.
C12M 1/00 (2006.01)
C12P 21/02 (2006.01)
C12M 1/26 (2006.01)

(52) U.S. Cl.
CPC ............ C12M 47/10 (2013.01); C12M 33/14 (2013.01); C12P 21/02 (2013.01)

(58) Field of Classification Search
None
See application file for complete search history.

(56) References Cited

U.S. PATENT DOCUMENTS

| 7,947,813 B2 | 5/2011 | Fahrner |
| 8,271,139 B2 | 9/2012 | Bellafiore |
| 8,679,778 B2 | 3/2014 | Laustsen |
| 2013/0280788 A1 | 10/2013 | Skudas |
| 2015/0232505 A1 | 8/2015 | Konstantinov |

FOREIGN PATENT DOCUMENTS

| EP | 2014760 | 1/2009 |
| EP | 2451963 | 4/2014 |
| WO | 2008153472 | 12/2008 |
| WO | 2010056584 | 5/2010 |
| WO | 2011003153 | 1/2011 |
| WO | 2012074481 | 6/2012 |
| WO | 2015075070 | 5/2015 |
| WO | 2015117883 | 8/2015 |
| WO | 2015117884 | 8/2015 |
| WO | 2015158696 | 10/2015 |

OTHER PUBLICATIONS

Sigma Aldrish: Antibody Basics, © 2011, 4pgs.*
Related PCT appln. No. PCT/EP2015/058037 (published as WO 2015/158696 AI), International Search Report and Written Opinion dated Jun. 17, 2015.
Related PCT Appln. No. PCT/EP2015/051801(published as WO2015/117884), International Preliminary Report on Patentability (IPRP), dated Aug. 9, 2016.
Related PCT Appln. No. PCT/EP2015/051801 (published as WO2015/117884), International Search Report, dated Apr. 28, 2015.
Related PCT Appln. No. PCT/EP2015/051797 (published as WO2015/117883), IPRP, Aug. 9, 2016.
Related PCT Appln. No. PCT/EP2014/075019 (published as WO2015/075070), IPRP, Jan. 23, 2015.
"Process Analytical Equipment for Monitoring, Control and Cost Optimization of Inline Dilution Processes turning science into solutions", Jan. 1, 2012 (Jan. 1, 2012), XP055118436, Retrieved from the Internet: URL:http://www.sartorius.de/fileadmin/fm-dam/sartorius_media/Bioprocess-Solutions/Process_Analytical_Technology/Application_Notes/ Appl_PAT_Equipment_for_Inline_Dilution_Processes_W-1125-e.pdf.
Response to EP Office Action for counterpart EP Appln. No. 15714846.1.
International Preliminary Report on Patentability for counterpart PCT Appln. No. PCT/EP2015/058037.
Response to EP Office Action for related EP Appln. No. 15714846.1 dated Jun. 8, 2017 (counterpart to U.S. Appl. No. 15/303,735).
Related PCT appln. No. PCT/EP2015/ 05 8037 (published as WO 2015/158696 AI), IPRP dated Oct. 18, 2016.
Related EP appln. No. EP15704231.8, amended claims dated Jun. 22, 2017 (counterpart to U.S. Appl. No. 15/117,019).
U.S. Appl. No. 15/117,019, Restriction Requirement dated Jun. 6, 2018, dated Sep. 7, 2018.
U.S. Appl. No. 15/117,019, Office Action dated Sep. 7, 2018, dated Sep. 7, 2018.
Related EP appln. No. EP15702220.3, response to written opinion, dated Apr. 6, 2017.
Related U.S. Appl. No. 15/117,059, Restriction Requirement dated Jun. 25, 2018.
U.S. Appl. No. 15/117,059, Office Action dated Sep. 18, 2018.
Related EP appln. No. 14 799795.1, communication dated Jun. 30, 2016 (counterpart to U.S. Appl. No. 15/037,765).
Related EP appln. No. 14 799795.1, response to communication dated Jun. 30, 2016, submitted Jan. 6, 2017 (counterpart to U.S. Appl. No. 15/037,765).
U.S. Appl. No. 15/037,765, Restriction Requirement dated Jun. 6, 2017.
U.S. Appl. No. 15/037,765, Office Action dated Nov. 6, 2017.

* cited by examiner

*Primary Examiner* — Thane Underdahl
(74) *Attorney, Agent, or Firm* — Cheryl H. Agris; Agris & von Natzmer, LLP

(57) ABSTRACT

The present invention relates to a high cell density fermentation fill and draw process for producing a product in a bioreactor system wherein during the fermentation, medium comprising impurities is removed via the impurity filter unit while new fresh medium is added to the cell culture vessel to replenish consumed nutrients and expelled medium.

20 Claims, 1 Drawing Sheet

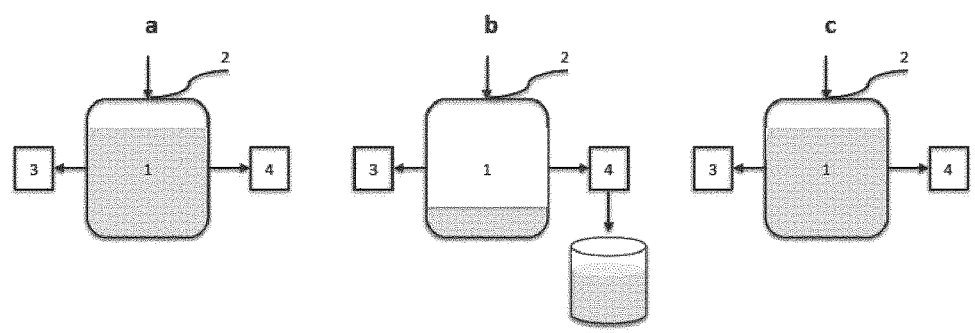

HIGH DENSITY FILL AND DRAW FERMENTATION PROCESS

FIELD OF THE INVENTION

The present invention relates to a high cell density fill and draw fermentation process. The methods of the present invention are suitable for preparing high cell density seed cultures and for use in a manufacturing process for preparing a polypeptide, in particular for preparing an active pharmaceutical ingredient for a pharmaceutical product.

BACKGROUND OF THE INVENTION

Traditionally, bacterial, yeast and mammalian cells for e.g. protein production are primarily cultured as suspension cultures in bioreactors, also called fermenters. In such bioreactors the environmental conditions can be precisely controlled by manipulating the supply of nutrients to the cells and the removal of impurities, and a stirring means may stir the culture medium within the reactor to provide for a homogeneous distribution of the cells.

The bioreactor may be operated as a closed system in a batch or fed-batch process or as a continuous system in a so-called chemostat or perfusion process.

In a batch operation the culture medium usually contains a medium with the necessary nutrients, for example glucose, vitamins, amino acids and minerals. During fermentation, these are consumed so that the medium becomes more and more deprived in nutrients. At the same time, the concentration of impurities increases, which ultimately results in inhibition of cell growth. In a fed-batch process one or more of the nutrients are fed (supplied) to the bioreactor during cultivation to achieve better growth conditions and higher cell densities. In repeated batch processes the cells left in the vessel after a harvest may be used as the inoculum for the next batch.

In a continuous system such as a chemostat fresh medium is continuously added, while medium comprising product, cells and impurities are continuously removed to keep the culture volume constant. By changing the rate at which medium is added to the bioreactor, the growth rate of the microorganism or cells can be controlled. For cells with a high growth rate such as yeast and bacterial cells, the chemostat typically removes cells from the medium along with the culture liquid in order to maintain a desired cell density.

A perfusion process is a special type of continuous process in which a suspension cell culture is continuously supplied with fresh medium to the bioreactor while spent culture media is continuously harvested. The cells are continuously filtered or otherwise separated from the harvest stream and returned to the bioreactor to maintain a uniform cell density. The constant addition of fresh medium and elimination of impurities provides the cells with the optimal environment to achieve high cell concentrations and thus higher productivity. This allows prolonging healthy cultures, potentially at high cell density, as well as a short residence time of the product in the bioreactor. This is more favourable for product quality and is required for the production of unstable polypeptides. Another advantage of the perfusion mode is that it allows the use of smaller bioreactors compared with fed-batch processes, which provides benefits such as reduced clean-in-place operation and the possibility to use disposable bioreactors instead of stainless steel reactors due to the smaller working volumes. Moreover, product may be continuously harvested by taking out medium (with product, cells and impurities) or via a so-called bleed.

A fill and draw process closely resembles a repeated batch fermentation. In batch fermentation the cells are grow in the culture vessel and the medium is harvested at the end of the run. In a fill and draw process the culture vessel is harvested before any of the nutrients become exhausted. Instead of removing all of the contents from the vessel, only a proportion of the tank volume is removed (typically 30%-80% of the tank volume). After the harvest, approximately the same volume of fresh medium is added back to the vessel. The cells are then allowed to grow in the vessel once more and another 30%-80% harvest is taken a set number of hours or days later.

The process may also be operated in two phases, with a first phase is operated identically to a simple batch process. After the first harvest, the culture vessel is again operated as a simple batch process; however, the length of the batch is shorter than the first batch because of the higher initial cell density. These short 'repeated batch phases' can be continued indefinitely. The culture vessel may be operated within a broad range of cycle times and a broad range of fill and draw volumes. EP2451963 describes such fill and draw processes for producing vitamin k-dependent proteins. However, EP2451963 does not disclose fill and draw processes using special bioreactors equipped with impurity filter units or specialized product harvest modules.

The present invention addresses the need for improved and more efficient utilization and handling of fill and draw cell culture processes in large-scale bioreactor systems.

SUMMARY OF THE INVENTION

The problem to be solved by the present invention is to provide a high cell density fill and draw fermentation process for improving cell densities and thereby increasing productivity of a bioreactor and the concentration of the product in the harvested medium, where productivity of a product (e.g. a seed culture or a polypeptide) can be improved due to e.g. optimized conditions for cell growth.

The solution is based on that the present inventor has found that by having a bioreactor with an impurity filter unit, which allows impurities with a molecular weight (MW) below the MW of the product, to be removed from the cell culture vessel while retaining the product inside a cell culture vessel, while fresh medium is added through a cell culture vessel inlet to replace or partly replace the medium removed through the impurity filter unit and culturing cells in the cell culture vessel to a high cell density and then perform a repeated draw and fill fermentation process one can obtain an increased cell density in the bioreactor during the fermentation process and in particular one can get a significant higher concentration of the product of interest in the harvested medium and thereby production economics that are superior to the production economics for comparable fermentation processes in bioreactors not having an impurity filter unit.

One aspect of the invention relates to a method for producing a product selected from a biopolymer expressed by a cell, a cell and a microorganism in a bioreactor system, wherein the bioreactor system comprises:

a cell culture vessel (1) comprising cells in a suitable medium;

a cell culture vessel inlet (2) for providing medium to the cell culture vessel (1);

an impurity filter unit (3), which allows impurities with a molecular weight (MW) below the MW of the product, to be removed from the cell culture vessel (1), while retaining the product inside the cell culture vessel (1) and wherein the impurity filter unit (3) is in fluid connection with the medium inside the cell culture vessel (1); and a harvest outlet (4), which allows the medium comprising the product and impurities to be removed from the cell culture vessel (1);

wherein the method comprises the following steps:

(a) fermenting the cells expressing the biopolymer, the cells or the microorganism in the cell culture vessel (1) in a suitable medium under suitable conditions and for a sufficient time until the cells expressing the biopolymer reach a specified cell density or the biopolymer reaches a specified concentration, the cells reach a specified cell density, or the microorganism reach a specified density of the microorganism, wherein during the fermentation, medium comprising impurities is removed via the impurity filter unit (3), and a first fresh medium is added through the cell culture vessel inlet (2) to replace or partly replace the medium removed through the impurity filter unit (3);

(b) removing a specified volume of the medium comprising the product and impurities from the cell culture vessel (1) through the harvest outlet (4), and (c) adding a second fresh medium to the cell culture vessel (1) via the cell culture vessel inlet (2) to replace or partly replace the medium removed through the harvest outlet (4) in step (b); and (d) optionally, during step (b), during step (c), or during both step (b) and step (c) removing the medium comprising impurities via the impurity filter unit (3), and adding a third fresh medium through the cell culture vessel inlet (2) to replace or partly replace the medium removed through the impurity filter unit (3);

(e) optionally, repeating step (b) and (c), (f) optionally repeating step (d), and (g) optionally, purifying the product, from the specified volume of medium comprising the product selected from the biopolymer expressed by the cell, the cell or the microorganism, and impurities.

Further objects of the present invention will become apparent in view of the present description, figures and claims.

BRIEF DESCRIPTION OF THE DRAWINGS

FIG. 1 is a schematic illustration of the method for producing a product in a bioreactor system of the present invention. In FIG. 1a is shown a cell culture vessel in expansion mode. In FIG. 1b, medium comprising product and impurities has been removed. In FIG. 1c, new fresh medium has been added to the cell culture vessel to replace consumed nutrients and expelled medium.

DEFINITIONS

Prior to a discussion of the detailed embodiments of the invention is provided a definition of specific terms related to the main aspects and embodiments of the invention. All terms are defined in accordance with the skilled person's normal understanding of the terms.

As used herein the term "biopolymer" refers to polypeptide, a protein or virus particle, which can be native or biologically or synthetically modified and includes fragments, multimers, aggregates, conjugates, fusion products etc.

As used herein the term "cell" encompass both prokaryotic and eukaryotic cells. As used herein the term "microorganism" intends to encompass all of the prokaryotes, namely the bacteria and archaea; and various forms of eukaryote, comprising the protozoa, fungi, algae, microscopic plants (green algae), and animals such as rotifers planarians and also virus.

As used herein the term "bioreactor" refers to any device or system that supports a biologically active environment. In one case but not limited to, a bioreactor is a vessel in which is carried out a chemical process which involves organisms or biochemically active substances derived from such organisms. This process can either be aerobic or anaerobic. Bioreactors are commonly cylindrical, ranging in size from some liters to cubic meters, and are often made of stainless steel but could also be made of other materials such as disposable materials.

A bioreactor may also refer to a device or system meant to grow cells or tissues in the context of cell culture. On the basis of mode of operation, a bioreactor may be classified as batch, fed-batch or continuous (e.g. continuous stirred-tank reactor model). An example of a bioreactor is the perfusion system. The bioreactor may be equipped with one or more inlets for supplying new fresh or concentrated medium to the cells, and with one or more outlets for harvesting product or emptying the bioreactor. Additionally, the bioreactor may be equipped with at least one outlet constructed in such a way that a separation device can be attached to the bioreactor. Typically the bioreactor's environmental conditions like gas (i.e., air, oxygen, nitrogen, carbon dioxide) flow rates, temperature, pH and dissolved oxygen levels, and agitation speed/circulation rate can be closely monitored and controlled.

As used herein the terms "impurities" refers to undesired chemical or biological compounds produced by cells or microorganisms present in the bioreactor, or which arise from cells or microorganisms that die or break open during the fermentation process. Impurities may include e.g. ethyl alcohol, butyl alcohol, lactic acid, acetone ethanol, gaseous compounds, peptides, lipids, ammonia, aromatic compounds, and DNA and RNA fragments, as well as media components or brake down products of the biopolymer.

As used herein the term "inlet" is intended to encompass any means that enables the introduction of fluid, such as medium, buffer, or water, into a cell culture vessel, a container, a tank or a unit and is an opening which is typically equipped with a fitting whereto for instance a tube or a valve can be connected.

As used herein the term "outlet" is intended to encompass any means that enables the fluid, such as medium, buffer, or water, to leave a cell culture vessel, a container, a tank or a unit and is an opening which is typically equipped with a fitting whereto for instance a tube or a valve can be connected.

The term "fluid" as used herein is intended to define any substance which flows and therefore includes liquids and gases which are able to flow. As used herein the term "in fluid connection" means that fluid, such as liquid, e.g. medium or buffer, can flow between a container, tank or unit (e.g. impurity filter unit) and an another container, tank, vessel or unit (e.g. cell culture vessel). The fluid connection may be interrupted by one or more valves and/or holding containers such that the flow of fluid through the fluid connection can be started and stopped whenever decided.

As used herein the term "medium" refers to a cell culture medium. Numerous cell culture media are known and commercially available. Such media typically have a composition which is adapted for cultivation of certain types of cells and may comprise salts, amino acids, vitamins, lipids, detergents, buffers, growth factors, hormones, cytokines, trace elements and carbohydrates.

As used herein the terms "fermentation", "fermenting the cells", and "culturing" refers broadly to the mass growth of cells and microorganisms in or on a growth medium. As used herein, fermentation, fermenting the cells and culturing may be used interchangeably and is a process by which cells are grown under controlled conditions, generally outside of their natural environment.

DETAILED DESCRIPTION OF THE INVENTION

The present inventor has found that by using a bioreactor system equipped with a impurity filter unit allowing impurities with a size below the size of the product, and medium to be removed from the cell culture vessel while new medium is added to the cell culture vessel to replace the medium removed through the impurity filter unit during a fill and draw fermentation process one can get a significant higher concentration of product of interest in the harvested medium as well as an increased productivity per liter spend medium. This process may also be called herein a high-density fill and draw fermentation process.

Product

As used herein a product refers to a biopolymer expressed by a cell, a cell and a microorganism.

Biopolymer refers to a polypeptide, a protein or a virus particle, which can be native or biologically or synthetically modified, including fragments, multimers, aggregates, conjugates, fusion products etc. In one embodiment, the biopolymer is a polypeptide such as a recombinant protein. As used herein, protein or polypeptide may be used interchangeably and refer to a chain of amino acids longer than about 30 amino acid residues. Proteins can exist as monomers or multimers, comprising two or more assembled polypeptide chains, fragments of proteins, polypeptides, oligopeptides, or peptides.

Examples of polypeptides of interest that may be produced using the methods of the invention include recombinant therapeutic proteins such as antibodies or fragments thereof, blood clotting factors, cytokines, enzymes, peptide hormones, etc. Specific examples of such proteins include human growth hormone, follicle-stimulating hormone, Factor VIII, Factor VII, Factor IX, erythropoietin (EPO), granulocyte colony-stimulating factor (G-CSF), alpha-galactosidase A, α-L-iduronidase (rhIDU; laronidase), N-acetylgalactosamine-4-sulfatase (rhASB; galsulfase), DNAse, tissue plasminogen activator (TPA), glucocerebrosidase, interferons (IF) such as interferon-α, interferon-β and interferon-γ, insulin, insulin derivatives, insulin-like growth factor 1 (IGF-1), tenecteplase, antihemophilic factor, human coagulation factor, and etanercept; and antibodies such as Trastuzumab, Infliximab, Basiliximab, Belimumab, Daclizumab, Adalimumab, Abciximab, Afutuzumab, Alemtuzumab, Cetuximab, Daclizumab, Denosumab, Eculizumab, Edrecolomab, Golimumab, Ibritumomab tiuxetan, Mepolizumab, Motavizumab, Natalizumab, Ofatumumab, Omalizumab, Oregovomab, Palivizumab, Pemtumomab, Pertuzumab, Ranibizumab, Rituximab, Tefibazumab and Zanolimumab.

In a further embodiment of the present invention the biopolymer is a recombinant protein such as an growth Human growth hormone, Follicle-stimulating hormone, Factor VIII, Factor VII, Factor IX Erythropoietin (EPO), Granulocyte colony-stimulating factor (G-CSF), Interferon (IF), Insulin, Insulin derivative, Insulin-like growth factor 1.

In a still further embodiment of the present invention the biopolymer is an antibody or a fragment thereof, where a fragment can e.g. be a Fab fragment, Fv fragment or single chain Fv (scFv) fragment, a blood clotting factor, a cytokine, an enzyme or a peptide hormone.

In a preferred embodiment of the present invention the product is a blood-coagulation factor such as blood-coagulation factor VIIa.

Polypeptides are typically expressed in mammalian cells under the control of regulatory sequences called promoter sequences. Cells expressing a polypeptide may be under the control of a constitutive promoter (i.e. unregulated sequences; this allows for continual transcription of the associated gene) or under control of an inducible promoter (regulatory sequences induced by the presence or absence of biotic or abiotic factors). An example of a constitutive promoter is a Chinese hamster EF-1α promoter. In one embodiment, the biopolymer is expressed under control of Chinese hamster EF-1α regulatory sequences.

By use of the bioreactor arrangement and method of the invention, it is possible to express polypeptides with high productivity. Thus, in one embodiment, the cells express a polypeptide, e.g. an antibody, and have a productivity of at least 1 gram/L/day, and preferably higher, such as 2 or 3 gram/L/day or more.

The isolated product (e.g. polypeptide) of interest produced using the system and method of the present invention may be purified by methods known in the art for the given product, formulated into a final commercially relevant composition of interest (e.g. a pharmaceutical composition), and packaged in a suitable container.

As used herein the product may also be a cell. The cell is the basic structural and functional unit of all known living organisms. There are two types of cells: eukaryotic and prokaryotic. Prokaryotic cells are usually independent, while eukaryotic cells can either exist as a single celled organism or be found in multicellular organisms. The prokaryote cell is simpler, and therefore smaller, than a eukaryote cell, lacking a nucleus and most of the other organelles of eukaryotes. There are two kinds of prokaryotes: bacteria and archaea; these share a similar structure. Plants, animals, fungi, slime molds, protozoa, and algae are all eukaryotic. The major difference between prokaryotes and eukaryotes is that eukaryotic cells contain membrane-bound compartments in which specific metabolic activities take place. Most important among these is a cell nucleus, a membrane-delineated compartment that houses the eukaryotic cell's DNA.

In one embodiment the product is selected from a cell, such as a mammalian cell.

In a further embodiment the cell expressing the biopolymer is at least one cell selected from the group consisting of *E. coli, Bacillus*, yeast of the genus of *Saccharomyces, Pichia, Aspergillus, Fusarium*, or *Kluyveromyces*, CHO (Chinese hamster ovary) cells, hybridomas, BHK (baby hamster kidney) cells, myeloma cells, HEK-293 cells, PER.C6® cells, amniosytes, including human amniosytes such as CAP® and CAP-T® cell lines, human lymphoblastoid cells and mouse cells, such as NSO cells.

In a still further embodiment the cell expressing the biopolymer is selected from a mammalian cell such as CHO, NSO, PER.C6®, BHK, or HEK.

As used herein a microorganism include all of the prokaryotes, namely the bacteria and archaea; and various forms of eukaryote, comprising the protozoa, fungi, algae, microscopic plants (green algae), and animals such as rotifers planarians and also virus. In one embodiment of the invention the microorganism is selected from fungus, yeast, humicola, *saccharomyces, aspergillus, bacillus, lactobacillus*.

As used herein the product may be a virus. A virus is a small infectious agent that only replicate inside the living cells of an organism. Viruses can infect all types of organisms, from animals and plants to bacteria and archaea. Viral populations do not grow through cell division, because they are a-cellular. Instead, they use the machinery and metabolism of a host cell to produce multiple copies of themselves, and they assemble inside the cell. Vaccination may be an effective way of preventing infections by viruses. Vaccines can consist of live-attenuated or killed viruses, or viral proteins (antigens). Live vaccines contain weakened forms of the virus, which do not cause the disease but, nonetheless, confer immunity. Such viruses are called attenuated. Biotechnology and genetic engineering techniques are used to produce subunit vaccines. These vaccines use only the capsid proteins of the virus. Hepatitis B vaccine is an example of this type of vaccine. In an embodiment of the present invention the product is a virus or a part of a virus.

Bioreactor

As used herein a bioreactor refers to any device or system that supports a biologically active environment, for example for cultivation of cells for production of a biological product. Bioreactors may range in size from a few liters to several cubic meters (i.e. several 1000 liters), and may be a conventional bioreactor based on a culture vessel of e.g. stainless steel or glass or a "single-use" bioreactor based on a disposable material such as a disposable bag.

While bioreactors have in the past typically been of the conventional type, most often based on stainless steel tanks, disposable bioreactors based on a disposable bag, typically made of a multilayer plastic material, are becoming more prevalent. For agitation, some single-use bioreactors use stirrers similar to those of conventional bioreactors, but with stirrers integrated into the plastic bag, while other single-use bioreactors are agitated by means of a rocking motion. Stirred single-use bioreactors may have a volume of up to several thousand liters, e.g. 2000 to 5000 liters, while rocking single-use bioreactors typically have a volume of up to about 1000 liters.

Single-use bioreactors have several advantages compared to conventional bioreactors, including reduced cleaning and sterilization demands, along with significant accompanying cost savings. In addition, complex qualification and validation procedures for pharmaceutical production can be simplified, and there is a reduced risk of cross contamination. Further, since single-use bioreactors contain fewer parts compared with conventional bioreactors, initial and maintenance costs are reduced.

Based on the mode of operation, a bioreactor may be classified as batch, fed-batch or continuous. Examples of continuous bioreactors are a chemostat and a perfusion bioreactor. The bioreactor is typically equipped with one or more inlets for supplying culture medium to the cells, and with one or more outlets for harvesting product or emptying the bioreactor. Additionally, the bioreactor may be equipped with at least one outlet constructed in such a way that an impurity filter unit can be attached to the bioreactor. Typically, the bioreactor's environmental conditions such as gas (i.e., air, oxygen, nitrogen, carbon dioxide) flow rates, temperature, pH and dissolved oxygen levels, and agitation speed/circulation rate can be closely monitored and controlled.

The bioreactor may optionally also include a separate inlet for adding components such as vitamins or growth factors. In this case, such components may be added to the cell culture vessel in addition to the medium, and may be either in concentrated or diluted form.

Cell Culture Vessel

A "cell culture vessel" as used herein refers to an integral part of a bioreactor system in which cells are grown under suitable conditions in a suitable medium. The cell culture vessel may be a single-use vessel, e.g. a disposable bag, or a conventional reusable vessel, typically a stainless steel or glass vessel, as explained above. Stainless steel vessels are typically configured with predefined port assemblies, whereas single-use bags use pre-sterilized plastic cultivation chambers that are discarded after use. This eliminates space-consuming and expensive clean-in-place (CIP) and steam-in-place (SIP) installations while reducing production turnaround times.

The cell culture vessel of the invention typically has a volume of at least 50 L, preferably at least 100 L, more preferably at least 250 L, and still more preferably at least 500 L. In many cases, the volume will be still higher, e.g. at least 1000 L or at least 2000 L.

In one embodiment of the present invention the method comprises fermenting the cells expressing the biopolymer, the cells or the microorganism in the cell culture vessel (1) in at least 50 L, such as in at least 75 L, such as in at least 100 L, such as in at least 200 L, such as in at least 300 L, such as in at least 500 L of suitable medium.

Impurity Filter Unit

Numerous specialized filters and filtration methods have been developed to separate materials according to their chemical and physical properties. Known filters include flat surface filters, pleated filters, multi-unit cassettes, and tubular forms such as hollow fibers. For the invention described herein any system of ultrafiltration technology can be applied as long as sterility can be ensured.

Examples of filtration systems applicable for use in the production of polypeptides and removal of impurities as described herein are systems such as cartridge systems, plate and frame systems, and hollow fiber systems. The systems can be operated by pumping liquid over the membrane, by vibration (e.g. as supplied by PallSep™) or by alternating tangential flow (ATF), and both polymeric and ceramic membranes are well suited for the filtration process. A skilled person will be able to select a membrane with suitable properties.

Hollow fiber membranes have been successfully employed in a wide variety of industries, and have several benefits that include high membrane packing densities the ability to withstand permeate back-pressure, thus allowing flexibility in system design and operation. Hollow fiber cartridges can operate from the inside to the outside during filtration, allowing process fluid (retentate) to flow through the center of the hollow fiber and permeate to pass through the fiber wall to the outside of the membrane fiber. Tangential flow can help limit membrane fouling. Other operating techniques that can be employed with hollow fiber membrane systems include back flushing with permeate and retentate reverse flow.

Accordingly, the impurity filter unit may be located in an external filter module attached to the bioreactor. Alternatively, the impurity filter may be located inside the bioreactor. The filter unit can also contain pumps or systems for preventing fouling of the filter such as an ATF system or the PallSep™ system in which controlled horizontal oscillation moves the membrane elements through the feed fluid. The oscillation generates vibrational energy at the membrane surface, giving shear (higher than that typically generated in conventional tangential flow filtration systems) that is limited to a small boundary layer above the membrane surface, and which is not applied to the bulk of the fluid. This ensures that even in high solids feed streams, the membranes do not cake with the retained species.

In one embodiment, the impurity filter unit is selected from a membrane filter, a gravitational separation unit and a centrifugal separation unit.

The skilled person will be able to select a suitable filter type for removal of impurities and a suitable membrane nominal molecular weight cutoff (NMWC) pore size with respect to allowing impurities to perfuse out of the impurity filter and harvest the polypeptide of interest through the product harvesting outlet.

The impurity filter is often selected with an NMWC within the range of 1000 to 30,000 (1-30 kDa), such as in the range of 2000 to 20,000 (2-20 kDa) or in the range of 2000 to 15,000 (2-15 kDa). However, if the product is a cell an impurity filter may be selected with an NMWC in the range of 1000 to 500,000 (1-500 kDa), but normally it is preferred that the impurity filter has a cutoff of less than 20,000 (20 kDa). Thus, in one embodiment the impurity filter unit is a membrane filter having an NMWC pore size of at least 1000, such as within the range of 2000 to 15,000.

In one embodiment of the present invention the impurity filter has a pore size with a nominal molecular weight cut-off (NMWC) with a maximum of at least 10%, such as of at least 20%, such as of at least 30%, such as of at least 40%, such as of at least 50% of the molecular weight of the biopolymer.

In another embodiment the impurity filter unit is a membrane filter having a molecular weight cut-off (NMWC) pore size of a maximum of 80% of the molecular weight (MW) of the product (e.g. polypeptide) of interest. For instance if the MW of the polypeptide of interest is 100,000 (100 kDa) the preferred maximum cut-off of the impurity filter will in this case be 80,000 (80 kDa). More preferably, the impurity filter has an NMWC pore size of a maximum of 50% of the MW of the polypeptide of interest. Thus, in one embodiment the impurity filter has a molecular weight cut-off (NMWC) pore size of a maximum of 80% of the MW of the biopolymer, such as a maximum of 50%.

During an extended run, it is possible to change the filters and resterilize the system without terminating the fermentation.

Harvest Outlet

In one embodiment the harvest outlet is in its most simple form just an outlet leading to a container or bag suitable for collecting the product along impurities and medium for storage or further downstream processing. The harvest outlet may also be in fluid connection with a separation device capable of, for example, separating biopolymer from cells, cell debris and impurities larger than the biopolymer.

When the cells present in the bioreactor reach a satisfactory cell density or when there is sufficient product present in the outflow through the harvesting outlet, harvest of the product may be initiated. This may be determined by measuring the cell density, for example using a spectrophotometer, or by measuring the amount of the product of interest by known means, for example using a suitable protein assay method in the case of a polypeptide product.

Cell Culture Medium

As used herein medium generally refers to a cell culture medium. Numerous cell culture media are known and commercially available. Such media typically have a composition which is adapted for cultivation of certain types of cells and may comprise salts, amino acids, vitamins, lipids, detergents, buffers, growth factors, hormones, cytokines, trace elements and carbohydrates. Examples of salts include magnesium salts, for example $MgCl_2 \times 6H_2O$, and iron salts, for example $FeSO_4 \times 7H_2O$, potassium salts, for example $KH_2PO_4$, KCl, sodium salts, for example $NaH_2PO_4$ or $Na_2HPO_4$, and calcium salts, for example $CaCl_2 \times 2H_2O$. Examples of amino acids are the 20 naturally occurring amino acids, for example histidine, glutamine, threonine, serine, methionine. Examples of vitamins include ascorbate, biotin, choline, myo-inositol, D-panthothenate and riboflavin. Examples of lipids include fatty acids, for example linoleic acid and oleic acid. Examples of detergents include Tween® 80 and Pluronic® F68. An example of a buffer is HEPES. Examples of growth factors/hormones/cytokines include IGF, hydrocortisone and (recombinant) insulin. Examples of trace elements include Zn, Mg and Se. Examples of carbohydrates include glucose, fructose, galactose and pyruvate. Examples of other components that may be included in the medium are soy peptone and ethanol amine. The skilled person will be familiar with suitable media and media supplements as well as suitable conditions with respect to specific expression cells and polypeptides of interest.

Silicon-based antifoams and defoamers or nonionic surfactants such as coblock polymers of ethylene oxide/propylene oxide monomers may be added to the medium during fermentation.

The pH, temperature, dissolved oxygen concentration and osmolarity of the cell culture medium will depend on the particular type of cell, and will be chosen such that they are optimal for the growth and productivity of the cells in question. The person skilled in the art will know how to determine the optimal conditions such as pH, temperature, dissolved oxygen concentration and osmolarity for a given culture. Usually, the optimal pH for mammalian cells is between 6.6 and 7.6, the optimal temperature is between 30 and 39° C., and the optimal osmolarity is between 260 and 400 mOsm/kg. For microbial systems the pH may be between 3 and 8 and the temperature from 20 to 45° C.

The solubility of the different medium components varies considerably, as many of the components will have a high solubility and thus be easily dissolved in water whereas other components such as certain vitamins, amino acids, lipids and growth factors have a low solubility in water. For this reason, cell culture media are normally prepared by mixing together all the components as a ready-to-use composition.

In one embodiment of the present invention the first, second and optionally third fresh medium are made from different components having different concentrations In another embodiment the first, second and optionally third fresh medium are selected from the same composition of medium.

The first, second and optionally third fresh medium is normally pre-heated to the same temperature as the medium that have been removed from cell culture vessel through the impurity filter (3) or the product harvest outlet (4) and is normally added to the cell culture vessel immediately after the removal.

Since the invention as described preferably operates using a high cell density, one may advantageously use a cell culture medium with a high cell density from one fermentation to re-start (i.e. seed) a new fermentation. A high viable cell density in this context is typically a density of at least 10 million cells/ml, preferably at least 20 million cells/ml, more preferably at least 30 million cells/ml, e.g. at least 40 million cells/ml, such as at least 50 million cells/ml.

Fermentation Process

Initiation of the fermentation process normally occurs by adding a cell culture with a high cell density to the medium in the cell culture vessel (i.e. seed). During the start of the fermentation when the level of product and impurities are low the impurity filter unit may be closed such that no liquid pass through the impurity filter unit. When the cell density increases and thereby also the levels of impurities, perfusion of liquid out through the impurity filter unit may be initiated and new fresh medium may be supplied with the same rate to the cell culture vessel as the rate of medium through the impurity filter unit to replenish consumed nutrients and expelled medium. The cells are then grown for a sufficient time until the cells reach a specified cell density before medium with product, cells and impurities will be removed.

In one embodiment the product is selected from a biopolymer expressed by a cell. In another embodiment the product is selected from a cell. In a further embodiment the product is selected from a microorganism.

As used herein sufficient time for fermenting the cells in step (a) will depend on the growth rate of the cells, the size of the cell culture vessel and the amount of cell culture for seeding the fermentation.

In one embodiment of the invention sufficient time for fermenting the cells in step (a) may be such as for 1 to 3 days, such as for 4 to 5 days, such as for 6 to 7 days, such as for 8 to 9 days or even longer.

When the cells present in the bioreactor reach a satisfactory cell density or when there is sufficient product present in the outflow through the harvesting outlet, harvest of the product may be initiated. This may be determined by measuring the cell density, for example using a spectrophotometer, or by measuring the amount of the product of interest by known means, for example using a suitable protein assay method in the case of a polypeptide product.

In one embodiment of the present invention a specified cell density in step (a) is a cell density of at least 30 million cells/ml, preferably at least 40 million cells/ml, more preferably at least 50 million cells/ml, e.g. at least 60 million cells/ml, such as at least 70 million cells/ml, such as at least 80 million cells/ml.

In another embodiment a specified level of biopolymer in step (a) is a level of at least 0.010 g/L, such as at least 0.050 g/L, such as at least 0.10 g/L, such as at least 0.50 g/L, such as at least 1.0 g/L, such as at least 5.0 g/L.

In one embodiment of the present invention the method comprises during step (a), fermenting the cells expressing the biopolymer, the cells or the microorganism in the cell culture vessel (1) in a suitable medium under suitable conditions and for a sufficient time until the cells expressing the biopolymer reach a specified cell density or the biopolymer reaches a specified concentration, the cells reach a specified cell density, or the microorganism reach a specified density of the microorganism, without removing impurities via the impurity filter unit (3).

During the fermentation of cells in step (a) typically about 0.5-1 reactor volume per day of medium comprising impurities perfuse out through the impurity filter unit (3), which is replaced or partly replaced by adding a first fresh medium through the cell culture vessel inlet (2). The term "reactor volume" in this context will be understood as corresponding to the working cell culture vessel volume of the particular system.

As used herein, replaced or partly replaced, refers to that either the same volume of medium passing out through the harvest outlet (4) is replaced with a first fresh medium added through the impurity filter unit (3) or in some cases it can be an advantages to only partly replaced the volume of medium passing out through impurity filter unit (3) with a second fresh medium added through the cell culture vessel inlet (2) since this can be a method to control the amount of product in the cell culture vessel e.g. the amount of biopolymer, or the cell density of the cell or the density of the microorganism.

In one embodiment of the invention in step (a) at least 60%, such as at least 60%, such as at least 70% such as at least 80% such as at least 90% of the first fresh medium is added through the cell culture vessel inlet (2) to partly replace the medium removed through the impurity filter unit (3).

In another embodiment the first fresh medium is added through the cell culture vessel inlet (2) to replace the medium removed through the impurity filter unit (3) in step (a).

In a further embodiment the method comprises in step (a) that the cells expressing the biopolymer reach a cell density, which cell density is higher than the cell density obtainable with the bioreactor system without the impurity filter unit (3) under identical conditions.

In a still further embodiment the method comprises in step (a) that the cells reach a cell density, which cell density is higher than the cell density obtainable with the bioreactor system without the impurity filter unit (3) under identical conditions.

In a further embodiment the method comprises in step (a) that the microorganism reach a cell density, which cell density is higher than the cell density obtainable with the bioreactor system without the impurity filter unit (3) under identical conditions.

When in step (a) the cells expressing the biopolymer reach a specified cell density or the biopolymer reaches a specified concentration, the cells reach a specified cell density, or the microorganism reach a specified density of the microorganism a specified volume of medium comprising the product and impurities is removed from the cell culture vessel (1) through the harvest outlet (4).

The specified volume of the medium comprising the product and impurities that are removed from the cell culture vessel may be determined by the skilled person taking into consideration the characteristics of the individual bioreactor system and the cell line. Typically, it will be in the range of from about 30% to about 80% of the medium in the cell culture vessel e.g. from about 0.3 to about 0.8 reactor volumes.

In one embodiment of the present invention the method comprises in step (b) removing at least 30%, such as at least 40%, such as at least 50%, such as at least 60% such as at least 70% such as at least 80% of the medium comprising the product and impurities from the cell culture vessel (1) through the product harvest module (4).

After the specified volume of the medium comprising the product and impurities have been removed from the cell culture vessel in step (b) a second fresh medium is added to the cell culture vessel (1) via the cell culture vessel inlet (2) in step (c) to replace or partly replace the medium removed through the harvest outlet (4) in step (b).

As used herein, replaced or partly replaced, refers to that either the same volume of medium passing out through the harvest outlet (4) is replaced with a second fresh medium added through the cell culture vessel inlet (2) or in some cases it can be an advantages to only partly replaced the volume of medium passing out through the harvest outlet (4) with a second fresh medium added through the cell culture vessel inlet (2) since this can be a method to control the amount of product in the cell culture vessel e.g. the amount of biopolymer, or the cell density of the cell or the density of the microorganism.

In one embodiment of the invention in step (c) at least 60%, such as at least 60%, such as at least 70% such as at least 80% such as at least 90% of the second fresh medium is added through the cell culture vessel inlet (2) to partly replace the medium removed through the harvest outlet (3) in step (b).

In another embodiment the second fresh medium is added through the cell culture vessel inlet (2) to replace the medium removed through the harvest outlet (3) in step (b).

According to the present invention step (b) and (c) may be repeated for at least 2 to 20 times without removing impurities via the impurity filter unit (3).

In a further embodiment the method further comprises step (e) wherein step (b) and (c) are repeated from at least 2 to 30 times.

In a still further embodiment the method comprises preceding step a), fermenting the cells expressing the biopolymer, the cells or the microorganism in the cell culture vessel (1) in a suitable medium under suitable conditions and for a sufficient time until the cells expressing the biopolymer reach a specified cell density or the biopolymer reaches a specified concentration, the cells reach a specified cell density, or the microorganism reach a specified density of the microorganism, without removing impurities via the impurity filter unit (3).

After several cycles of removing medium comprising the product and impurities from the cell culture vessel through the harvest outlet (4) and adding new medium via the cell culture vessel inlet (2) the level of impurities may start to accumulate in the cell culture vessel with an increasing rate. In such a scenario it may be an advantage to remove medium comprising impurities via the impurity filter unit, and adding a third fresh medium through the cell culture vessel inlet (2) to replace or partly replace the medium removed through the impurity filter unit (3) during step (b), during step (c) or during both step (b) and step (c).

In one embodiment of the invention the method further comprises step d).

In another embodiment of the invention the method comprises in step (d) that the third fresh medium is added through the cell culture vessel inlet (2) to replace the medium removed through the impurity filter unit (3).

In a further embodiment of the invention in step (d) at least 50%, such as at least 60%, such as at least 70% such as at least 80% such as at least 90% of the third fresh medium is added through the cell culture vessel inlet (2) to partly replace the medium removed through the harvest outlet (3) during step (b), during step (c) or during both step (b) and step (c).

In a further embodiment the method comprises step (f) wherein step (d) is repeated from at least 2 to 30 times.

Depending on the cell type and the growth conditions, cells may double within less than 1 hour and up to several days. Mammalian cell lines may double every about 14 to 48 hours, but cell lines adapted to high yield expression of polypeptides in bioreactors typically double every from about 15 to about 36 hours. If the cells double every 24 hours, half (i.e. 0.5) of the reactor volume medium comprising product and impurities can be removed daily through the harvest outlet (4) and 0.5 of the reactor volume can be replaced with new fresh medium to replenish consumed nutrients and expelled medium and thereby keeping a constant productivity in the bioreactor system.

If the doubling time is faster than 24 hours more reactor volume medium comprising product and impurities can be removed daily and be replaced with new fresh medium. If the doubling time is slower than 24 hours less reactor volume can be removed daily while keeping a constant productivity in the bioreactor system. A skilled person knows how to select suitable cell lines and control cell growth for optimal production of product of interest.

Persons skilled in the art will be aware that the temperature of the medium in the cell culture vessel is a key factor for productivity of the cells, with a temperature in the range of about 30-38° C. often being optimal, and that it may be advantageous to employ a temperature reduction during the fermentation. Such procedures are well-known, in particular for mammalian cells such as CHO cells and typically involve an initial fermentation phase at a first temperature of e.g. about 37° in order to obtain a desired cell density, followed by a reduction in temperature to, for example, about 32-35° for the remainder of the fermentation in order to increase expression of the polypeptide product and reduce cell division.

In one embodiment of the present invention the method comprises in step (a) fermenting the cells in the cell culture vessel (1) in a suitable medium with a temperature in the range of about 30-38° C. and The process is continuously monitored as known in the art and as otherwise explained herein, such that growth conditions, medium concentration, cell density, pH etc. are maintained within desired specifications.

The product obtained by the present invention may be isolated form the medium and impurities.

If the product is cells or microorganisms they may be isolated by filtration centrifugation or sedimentation according to standard techniques. If the product is a biopolymer it may by purified by from cells and impurities by a clarification process followed by further purification using chromatography systems. A skilled person knows suitable techniques to purify the product of the present invention.

In one embodiment the method further comprises comprising step (g), purifying the product, from the specified volume of medium comprising the product selected from the biopolymer expressed by the cell, the cell or the microorganism, and impurities.

The method of the present invention may be particular usefully for operating several cell cultures vessels in series, such as two, such as three or more preferred 4 cell cultures vessels in a common unit also comprising a purification facility for purifying the product. In such a scenario, for example, 4 cell cultures vessels are operated such that culture vessel 4 functions for preparing seed cultures to the other culture vessels e.g. it is operated in expansion mode.

Cell culture vessel 1, 2 and 3 may then operated in a mode wherein the cells have a doubling time of about three days and wherein medium comprising product and impurities is removed from cell culture vessel 1 on day 1 and provided to the purification facility and the medium removed for purification is replaced with new fresh medium. Medium comprising product and impurities is removed from cell culture vessel 2 on day 2 and provided to the purification facility and the medium removed for purification is replaced with new fresh medium. Medium comprising product and impurities is removed from cell culture vessel 3 on day 3 and provided to the purification facility and the medium removed for purification is replaced with new fresh medium and this process is repeated for a number of cycles until the productivity of one of the culture vessel decreases to an unacceptable lever where after the cells in cell culture vessel is used for seeding a new fermentation and the process continues.

All patent and non-patent references cited in the present application are hereby incorporated by reference in their entirety.

Any combination of the above-described elements in all possible variations thereof is encompassed by the invention unless otherwise indicated herein or otherwise clearly contradicted by context.

The terms "a", "an" and "the" as used herein are to be construed to cover both the singular and the plural, unless otherwise indicated or clearly contradicted by context.

The invention claimed is:

1. A method for producing a product selected from:
    A) a biopolymer expressed by a cell,
    B) a cell, and
    C) a microorganism
    in a bioreactor system in a fill and draw process, wherein the bioreactor system comprises:
    a cell culture vessel (1) comprising cells or microorganisms in a suitable medium;
    a cell culture vessel inlet (2) for providing medium to the cell culture vessel (1);
    an impurity filter unit (3), which allows impurities with a molecular weight (MW) below the MW of the product, to be removed from the cell culture vessel (1), while retaining the product inside the cell culture vessel (1) and wherein the impurity filter unit (3) is in fluid connection with the medium inside the cell culture vessel (1); and
    a harvest outlet (4), which allows the medium comprising the product and impurities to be removed from the cell culture vessel (1);
    wherein the method comprises the following steps:
    (a) fermenting the cells expressing the biopolymer, the cells, or the microorganisms in the cell culture vessel (1) in a suitable medium under suitable conditions and for a sufficient time until;
        (i) the biopolymer reaches a specified concentration of at least 0.1 g/L,
        (ii) the cells reach a cell density of at least 40 million cells/ml, or
        (iii) the microorganisms reaches a specified cell density or density of the microorganisms is higher than that obtainable with the bioreactor system without the impurity filter unit (3) under identical conditions, wherein during the fermentation, medium comprising impurities is removed via the impurity filter unit (3), and a first fresh medium is added through the cell culture vessel inlet (2) to replace or partly replace the medium removed through the impurity filter unit (3);
    (b) removing a specified volume of the medium comprising the product and impurities from the cell culture vessel (i) through the harvest outlet (4) before nutrients in said medium become exhausted, and
    (c) after said removal of medium in step (b), adding a second fresh medium to the cell culture vessel (1) via the cell culture vessel inlet (2) to replace or partly replace the medium removed through the harvest outlet (4) in step (b); and
    (d) optionally, adding a third fresh medium through the cell culture vessel inlet (2) during step (b), during step (c), or during both step (b) and (c), after removing the medium comprising impurities via the impurity filter unit (3);
    (e) optionally, repeating step (b) and (c),
    (f) optionally repeating step (d), and
    (g) optionally, purifying the product, from the specified volume of medium comprising the product selected from the biopolymer expressed by the cell, the cell, or the microorganism, and impurities.

2. The method according to claim 1, wherein during step (a) fermenting the cells expressing the biopolymer, the cells, or the microorganisms in the cell culture vessel (1) in a suitable medium under suitable conditions and for a sufficient time until the biopolymer reaches a concentration of 0.1 g/L, the cells reach a cell density of 40 million cells/mL, or the microorganism reach a specified density before removing impurities via the impurity filter unit (3).

3. The method according to claim 1, wherein preceding step (a) fermenting the cells expressing the biopolymer, the cells, or the microorganism in the cell culture vessel (1) in a suitable medium under suitable conditions and for a sufficient time until the biopolymer reaches a concentration of 0.1 g/L, the cells reach a cell density of 40 million cells/mL, or the microorganisms reaches a specified density without removing impurities via the impurity filter unit (3).

4. The method according to claim 1, wherein the first, second and optionally third fresh medium are selected from the same composition of medium.

5. The method according to claim 1, further comprising step (d).

6. The method according to claim 1, further comprising step (e) wherein steps (b) and (c) are repeated from at least 2 to 30 times.

7. The method according to claim 1, further comprising step (f) wherein step (d) is repeated from at least 2 to 30 times.

8. The method according to claim 1, further comprising step (g), purifying the product, from the specified volume of medium comprising the product selected from the biopolymer expressed by the cell, the cell, or the microorganism, and impurities.

9. The method according to claim 1, wherein in step (a) fermenting in the cell culture vessel (1) is performed with at least 50 L of suitable medium.

10. The method according to claim 1, wherein in step (a) fermenting in the cell culture vessel (1) is performed until the cells reach a cell density of at least 50 million cells/ml.

11. The method according to claim 1, wherein in step (b) a specified volume of at least 30% of the medium comprising the product and impurities is removed from the cell culture vessel (i) through the product harvest module (4).

12. The method according claim 1, wherein the cell expressing the biopolymer is a mammalian cell.

13. The method according to claim 1, wherein the biopolymer is a recombinant protein.

14. The method according to claim 1, wherein the biopolymer is an antibody or a fragment thereof or a blood-coagulation factor.

15. The method according to claim 1, wherein the impurity filter has a pore size with a nominal molecular weight cut-off (NMWC) with a maximum of at least 10% of the molecular weight of the biopolymer.

16. The method according to claim 1, wherein in step (b) a specified volume of at least 50% of the medium comprising the product and impurities is removed from the cell culture vessel (1) through the product harvest module (4).

17. The method according to claim 1, wherein in step (b) a specified volume of at least 80% of the medium comprising the product and impurities is removed from the cell culture vessel (1) through the product harvest module (4).

18. The method according claim 1, wherein the cell expressing the biopolymer is a mammalian cell selected from a CHO, NSO, PER.C6®, BHK, or HEK cell.

19. The method according to claim 1, wherein the biopolymer is a recombinant protein selected from Human growth hormone, Follicle-stimulating hormone, Factor VIII, Factor VII, Factor IX Erythropoietin (EPO), Granulocyte colony-stimulating factor (G-CSF), Interferon (IF), Insulin, Insulin derivative or Insulin-like growth factor 1.

20. The method according to claim 1, wherein the impurity filter has a pore size with a nominal molecular weight cut-off (NMWC) with a maximum of at least 40% of the molecular weight of the biopolymer.

* * * * *